United States Patent [19]
Franzoni et al.

[11] Patent Number: 5,077,052
[45] Date of Patent: Dec. 31, 1991

[54] CHITOSAN DERIVATIVES USEFUL IN COMPOSITIONS FOR COATING FEEDSTUFF ADDITIVES INTENDED FOR RUMINANTS

[75] Inventors: Christine Franzoni; Christian Gagnieu, both of Lyon; Hugues Porte, Caluire, all off, France

[73] Assignee: Rhone-Poulenc Sante, Antony, France

[21] Appl. No.: 442,622

[22] Filed: Nov. 29, 1989

[30] Foreign Application Priority Data

Nov. 30, 1988 [FR] France ................. 88 15675
Nov. 30, 1988 [FR] France ................. 88 15676

[51] Int. Cl.$^5$ .......................... A61K 9/36; A61K 9/14; A61K 31/715; A61K 47/36
[52] U.S. Cl. .................... 424/438; 424/439; 424/442; 424/463; 424/489; 424/490; 424/493; 424/499; 514/55; 536/20; 106/162
[58] Field of Search ............. 424/438, 439, 442, 493, 424/499, 463, 489, 490; 536/20; 514/55; 106/162

[56] References Cited

U.S. PATENT DOCUMENTS 4,424,346  1/1984  Hall et al. ................ 536/20

FOREIGN PATENT DOCUMENTS 0013181  7/1980  European Pat. Off. ......... 536/20
0013512  7/1980  European Pat. Off. ......... 536/20
0345017  12/1989  European Pat. Off. ......... 536/20
63-20302  1/1988  Japan ....................... 536/20
1504237  8/1989  U.S.S.R. .................... 536/20

OTHER PUBLICATIONS

Agricultural and Biological Chemistry, vol. 47, No. 6, 1983, pp. 1389–1391.
Hirano et al.; Carbohydrate Research 65:166–168 (1978).
Fujii et al.; Carbohydrate Research 83:389–393 (1980).

Primary Examiner—Ronald W. Griffin
Assistant Examiner—Nancy S. Carson
Attorney, Agent, or Firm—Morgan & Finnegan

[57] ABSTRACT

Novel organosoluble derivatives of chitosan, useful in coating biologically active feedstuff additives intended for ruminants, to provide coatings which are stable at a pH greater than 5 and which release the biologically active substance at a pH below 3.5, consist of a random chain of units represented by the formulae:

$$\underset{(Ia)}{\begin{array}{c}CH_2-OR_1\\ \diagup O\\ OR_4\quad O\\ N=CHR_2\end{array}} \quad \text{and} \quad \underset{(Ib)}{\begin{array}{c}CH_2-OR_1\\ \diagup O\\ OR_4\quad O\\ NH-R_3\end{array}}$$

in which: $R_1$ represents an alkylcarbonyl radical (2 to 4 carbon atoms), $R_2$ represents an alkyl radical (2 to 21 carbon atoms) or an optionally substituted phenyl radical, and $R_3$ and $R_4$ represent a hydrogen atom or alkylcarbonyl radicals (2 to 4 carbon atoms).

28 Claims, No Drawings

CHITOSAN DERIVATIVES USEFUL IN COMPOSITIONS FOR COATING FEEDSTUFF ADDITIVES INTENDED FOR RUMINANTS

FIELD OF THE INVENTION

The present invention relates to chitosan derivatives, their preparation and their use in coating feedstuff additives or biologically active substances, intended for monogastric or polygastric animals.

BACKGROUND OF THE INVENTION

Chitosan is a basic polysaccharide, the average molecular weight of which is generally greater than 500,000, which is made up of $\beta$-2-amino-2-deoxy-D-glucopyranose residues bonded in the 1,4-position. Chitosan can be obtained by deacetylation of chitin, which itself can be extracted, for example, from the carapace of crustaceans where it is present in a significant quantity.

Because of its chemical structure, chitosan is resistant to hydrolysis at the oside bonds in a basic medium, is insoluble at a pH greater than 6.5, and soluble and hydrolyzable under acid conditions. Taking into account its film-forming properties, chitosan could be an agent of choice for the protection of various substances whose release must be controlled as a function of pH. However, chitosan has the drawback of being insoluble in the customary organic solvents, which makes it difficult to produce films or coating layers.

DESCRIPTION OF THE INVENTION

Novel derivatives of chitosan have now been found which are organosoluble and which preserve the property of forming films and of being sensitive to variations in pH, and it is this which is the subject of the present invention.

The novel chitosan derivatives of the invention consist of a random chain of units which can be represented by the following formulae:

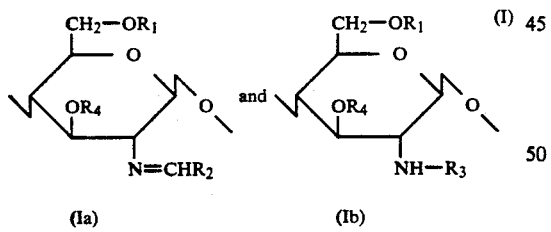

in which
- $R_1$ represents an alkylcarbonyl radical containing 2 to 4 carbon atoms,
- $R_2$ represents an alkyl radical containing 2 to 21 carbon atoms or a phenyl radical which is unsubstituted or substituted by one or more hydroxyl or alkoxy radicals, and
- $R_3$ and $R_4$ represent identical or different groups chosen from the alkylcarbonyl radicals containing 2 to 4 carbon atoms and hydrogen.

The chitosan derivatives of the invention preferably have an average molecular weight of between 10,000 and 80,000, and still more preferentially of between 10,000 and 20,000. A composition corresponding to: 60 to 100% of units of the formula (Ia) above, and 0 to 40% of units of the formula (Ib) is likewise preferred.

The chitosan derivatives of the invention which are preferred are those for which at least one and preferably several of the following conditions are met in the formulae (I):
- at least 50% of the units $R_1$ represent an acetyl radical,
- $R_2$ represents an alkyl radical containing 5 to 12 carbon atoms,
- at least 50% of the units $R_3$ represent an acetyl radical, and
- at least 50% of the units $R_4$ represent an acetyl radical.

The novel derivatives of chitosan are prepared, in accordance with a feature of the invention, by a process which comprises:
- in a first step, hydrolysing a chitosan having a degree of deacetylation greater than 80%,
- in a second step, condensing an aliphatic or aromatic aldehyde of formula $R_2CHO$ with the chitosan obtained from the first step, and
- in a third step, esterifying the chitosan obtained from the second step with an acid of formula $R_1$—OH or derivative thereof.

The deacetylation is carried out using chitin obtained from carapaces of animals by bringing it into contact with sodium hydroxide in aqueous solution for approximately 1 hour at about 135° C.

After the deacetylation and before the hydrolysis step it is advantageous to purify the chitosan by treatment with acetic acid, precipitation with a strong base, preferably sodium hydroxide, washing with water and with ethanol and then heating in ethanol to about 80° C. This technique enables technical grade chitosan to be purified.

According to a preferred method for carrying out the first step, the chitosan is hydrolyzed with a strong acid chosen from:
- hydrochloric acid,
- sulphuric acid,
- nitric acid, and
- supported mineral acids (TONSIL ® type).

Preferably, in this first step, about 25 to 50 g/liter of chitosan are introduced into a solution of strong acid of an acidity of 0.5N to 1N.

According to a preferred mode of operation, the hydrolysis is carried out at a temperature of between 80° and 120° C. and preferably at about 100° C. for 5 to 30 hours.

The hydrolyzed chitosan is then precipitated by rendering the mixture alkaline to a pH close to 10. It is separated by filtration.

The polysaccharides obtained after hydrolysis have an average molecular weight of, in particular, between 10,000 and 80,000 and very particularly between 10,000 and 20,000.

According to a preferred method for carrying out the second step, the hydrolyzed chitosan obtained from the first step is subjected to a condensation reaction with an aldehyde of formula:

$$R_2\text{—CHO} \qquad (II)$$

in which $R_2$ has the same meaning as above.

The condensation of the aldehyde and hydrolyzed chitosan is preferably carried out at a pH of between 5.5 and 6, in particular of about 5.5.

The solvent for the condensation reaction is preferably an aqueous-alcoholic medium containing an alcohol chosen from methanol, ethanol or isopropanol. The water/alcohol weight ratio is preferably between 0.45 and 0.65.

Aldehydes of formula (II) which are preferably used are the aliphatic aldehydes having 3 to 14 carbon atoms, such as:

propanol,
butanal,
pentanal,
hexanal,
heptanal,
decanal,
dodecanal,
tetradecanal.

For a better implementation of the invention it is preferred that the molar ratio of the aldehyde of formula (II) to the average oside monomer unit of chitosan is greater than 15 and preferably about 20.

According to a preferred mode of operation, the condensation reaction is carried out at between 10° and 50° C. and still more preferentially at between 10° and 30° C.

The product of the condensation reaction between the aldehyde and the chitosan obtained from the second step of the process of the invention is extracted, in particular, by means of organic solvents chosen from:

ketones such as acetone,
alcohols such as ethanol.

The third step of the process of the invention consists in esterifying the modified chitosan obtained from the second step.

The esterification of the modified chitosan obtained from the second step may be effected with an acid or an acid derivative of formula:

$$(RCO)_n A \qquad (III)$$

in which:

n is 1 or 2,
A is a hydroxyl group or a halogen when n=1,
A is oxygen when n is 2, and
R represents an alkyl group having one to three carbon atoms.

The acylation is preferably carried out with an acid or an acid derivative of formula (III) in which R is an alkyl group containing 1 to 3 carbon atoms and very particularly in which R is the —$CH_3$ group.

Amongst the acid derivatives of formula (III) the acid anhydrides are preferably used and very preferentially acetic anhydride.

The acylation reaction is preferably carried out in an organic solvent such as a pyridine.

When the reaction is carried out between an acid halide and chitosan, it is preferred to add a base so as to neutralize the hydracid formed, or a basic organic solvent such as, for example, the pyridines, can be used.

The acylation is carried out, in particular, at a temperature of between 10° and 50° C. and preferably at a temperature of between 10° and 30° C.

The modified chitosan obtained from the third step is recovered, for example, by evaporating off the reaction solvent, washing the residue with alkaline medium, taking up the insoluble product in acetone, and removing the insoluble matter by centrifuging.

The chitosan obtained has an average molecular weight of, in particular, between 10,000 and 110,000 and very particularly of between 10,000 and 25,000.

The modified chitosan can be used:

as a component in cosmetic preparations,
as a sequestering agent for heavy metals with the formation of an insoluble complex,
for the preparation of films, filaments, fibres and coatings,
for coating feedstuff additives or biologically active substances intended for feeding ruminants.

The chitosan derivatives according to the present invention are soluble in the customary organic solvents, such as acetone, ethanol or methylene chloride. Chitosan derivatives of very particular interest are those made up of the random arrangement of the units of general formulae (Ia) and (Ib) in which $R_2$ represents an alkyl radical containing 2 to 13 carbon atoms, and more particularly 6 to 9 carbon atoms, the degree of fixation of the aldehyde is between 55 and 65% relative to the oside monomers of chitosan, $R_1$ represents an acetyl radical, $R_3$ represents a hydrogen atom or an acetyl radical and some of the radicals $R_4$ represent a hydrogen atom and the others an acetyl radical.

For example, the solubility in organic liquids which corresponds to the fraction of organosoluble products in a crude product obtained from the reaction chain can be determined by placing 10 g of ground crude acetylation product in 100 g of solvent and measuring the amount of product which dissolves.

The chitosan derivatives according to the invention are particularly useful for preparing compositions for coating feedstuff additives or biologically active substances which are intended in the main for ruminants, which are stable in a medium which has a pH equal to or greater than 5.5 and which permit the release of the feedstuff additive or the biologically active substance in a medium which has a pH less than or equal to 3.5.

When certain biologically active substances (medicaments, vitamins or amino acids) are administered to ruminants an enzymatic destruction of these substances, promoted by the residence time (a few hours to several days) and by the pH (between 5 and 6), takes place during the passage through the rumen. The result is that the active substance which is degraded loses the major part of its efficacy before it arrives in the abomasum and the intestine of the ruminant.

It is therefore important to be able to protect these biologically active substances by coatings which are stable in the rumen of ruminants, that is to say which are stable to degradation by the microorganisms and which permit the release of the biologically active substances in a part of the digestive system, more particularly the abomasum, in which the pH is less than or equal to 3.5. Although the duration of protection in the rumen must be relatively long (a few hours to several days), the release of the active substance in the abomasum must take place within a relatively short time (a few minutes to a few hours).

The novel chitosan derivatives according to the present invention can be used as pH-sensitive substances in coating compositions for feedstuff additives or biologically active substances intended for ruminants. In particular, the novel organosoluble chitosan derivatives can advantageously wholly or partially replace the synthetic pH-sensitive substances such as the basic copolymers, such as copolymers of styrene with vinylpyridines, which are customarily used in this type of composition.

The chitosan derivatives according to the invention, which are obtained from natural products acceptable in feedstuffs, are hydrolyzed in the organism to substances which are non-toxic to the animals, which constitutes a considerable practical advantage.

More particularly, the novel chitosan derivatives can be used as pH-sensitive substances in the coating compositions which are the subject of French Patents 2,514,261, 2,582,909, 2,575,039, 2,575,040, 2,603,458 or 2,606,597 and they can be employed in the same way.

EXAMPLES

The following examples illustrate the present invention.

EXAMPLE 1

1-Purification of the chitosan

Technical grade chitosan (from the company SIGMA) (40 g) is dissolved in a 4% (wt./vol.) aqueous acetic acid solution (3 liters). The solution is filtered through a sieve which has a mesh of 125 microns. The chitosan is precipitated by adding a 25% aqueous sodium hydroxide solution until the pH is 9-11, then separated off by filtration and then washed on the sieve with distilled water and finally with absolute ethanol. The fibrous precipitate is pressed to extract the maximum of solvent and is then dispersed in absolute ethanol (1 liter). The mixture is heated at 80° C. for 2 hours. After filtering off, the purified chitosan is dried under reduced pressure at 60° C. Purified chitosan (35 g) is thus obtained which has the following characteristics:

infrared spectrum (determined using tablets as a mixture with KBr): main characteristic absorption bands at 3,400, 2,900 and 1,650 cm$^{-1}$ average molecular weight: greater than 500,000.

The average molecular weight is determined by high performance liquid chromatography using 5 columns 50 cm long filled with glycophase G/CPG (N. D. Pierce) of porosity 3125 (2 columns), 1902, 1038 and 547 Å. The mobile phase is a 0.2M sodium acetate and 0.33M acetic acid buffer of pH 4.2. The flow rate is 1 cc/minute and the detection is carried out by refractometry. The calibration is carried out using standard solutions of dextran (from the company SIGMA) with a molecular weight of 506,000 to 110,000.

percentage of deacetylation: 80% of the oside rings of the purified chitosan contain a free primary amine function.

The percentage of deacetylation is determined in the following way: a sample of chitosan reduced to powder (particles about 20 microns in size) is suspended in a water/dimethyl sulphoxide mixture (9/1 by volume), the pH of which is brought to 11 by the addition of 0.1N sodium hydroxide solution. The potentiometric determination is carried out using 0.1N hydrochloric acid.

Elementary analysis: C %=40.90 H %=6.76 N %=7.52 O %=44.82.

2-Acid hydrolysis of the purified chitosan

Purified chitosan (25 g) is dissolved in 0.5N hydrochloric acid (650 cc). The solution is heated in an oil bath at 98° C. for 18 hours. After cooling, the chitosan is precipitated slowly by adding 5N sodium hydroxide solution until the pH of the reaction mixture reaches 10. The salts formed are removed by dialysis. The purified chitosan is separated off by filtration or centrifuging, washed with absolute ethanol and then dried under reduced pressure at 60° C. Hydrolyzed chitosan (21 g) is thus obtained which has the following characteristics:

average molecular weight: close to 13,000 (determination under the conditions described above using 4 columns 50 cm long filled with glycophase G/CPG (N. D. Pierce) of porosity 1902, 1038, 547 and 242 Å and standard solutions of dextran (from the company SIGMA) with a molecular weight of 110,000 to 9,000).

Elementary analysis: C %=40.13 H %=6.76 N %=7.72 O %=45.39.

3-Condensation of decanal with hydrolysed chitosan

Hydrolyzed chitosan (1 g) is dissolved in a 10% aqueous acetic acid solution (20 cc). The pH is adjusted to 4.5 by adding a 5N sodium hydroxide solution and methanol (40 cc) and decanal (23 cc) are then added. The viscous reaction mixture is stirred for 18 hours at a temperature close to 20° C. The condensation product is extracted with acetone in a Soxhlet apparatus for 5 hours. After drying under reduced pressure at 35° C., the decanal/chitosan condensation product is obtained (1.48 g) which has the following characteristics:

infrared spectrum (determination using tablets as a mixture with KBr): main characteristic absorption bands at 3450, 2930 and 2860 cm$^{-1}$ percentage of fixation of the decanal: 60-65%.

The determination is carried out after reduction of the imine bond by sodium borohydride in an ethanol/water medium (1/1 by volume). The percentage of secondary amine groups is determined by potentiometric determination of the reduced derivative dissolved in an acetic acid/ethanol medium (2/1 by volume), titrating with 0.1N perchloric acid.

4-Acetylation of the decanal/chitosan condensation product

The decanal/chitosan condensation product (1 g) is dispersed in anhydrous pyridine (25 cc). Acetic anhydride (5 cc) is added. The reaction mixture is stirred for 24 hours at a temperature close to 20° C. After evaporating off the pyridine, the residue is taken up twice in toluene and then suspended in pentane. The suspension is filtered and the solid is washed 3 times with a 0.1N sodium hydroxide solution and then rinsed with distilled water until neutral. After transfer to a round-bottomed flask, the product is dried by entraining the water with acetone.

The product obtained is purified by centrifuging at 16,000 revolutions/minute after dissolving in acetone (50 cc). After evaporating off the supernatant liquor, the residue obtained is washed on a No. 3 glass frit with diethyl ether.

Product (1.075 g) of general formula (I) made up of a random arrangement of the units of formula:

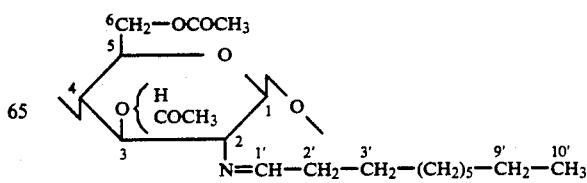

-continued

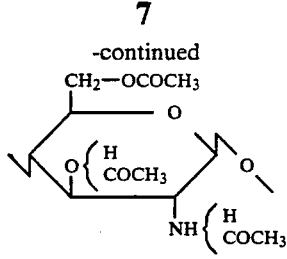

Examination with the electron microscope does not reveal any crack or porosity in the film both without plasticizer and with plasticizer.

EXAMPLES 2 TO 6

The procedure of Example 1 is followed, using 1 g of hydrolyzed chitosan and employing different aliphatic aldehydes; the results obtained are collated in Table 2.

TABLE 2

| Examples | Aldehyde | Percentage of fixation of the aldehyde | Weight of the aldehyde/chitosan condensation product | Weight of the acetylated aldehyde/chitosan condensation product |
| --- | --- | --- | --- | --- |
| 2 | propanal (9 cc) | 69 | 1.20 g | 0.160 g |
| 3 | pentanal (13 cc) | 63 | 1.36 g | 0.580 g |
| 4 | heptanal (17 cc) | 61 | 1.49 g | 0.965 g |
| 5 | dodecanal (27 cc) | 58 | 1.70 g | 0.900 g |
| 6 | tetradecanal (25 g) | 59 | 1.82 g | 0.600 g | is thus obtained which has the following characteristics:
percentage of fixation of the aldehyde: 60–65%
percentage of acetylamino: 20 to 35–40%
infrared spectrum (determination using tablets as a mixture with KBr): main characteristic absorption bands at 3400, 2920–2830, 1750–1230, 1680, 1640 and 1540 cm$^{-1}$
$^{13}$C magnetic resonance spectrum (90 MHz-deuterated chloroform-shift in ppm): 170 (CO of the acetyl)-169 (CH=N)-102 (1-C)-72.73 and 75.5 (2-C, 3-C, 4-C and 5-C)-62.5 (6-C)-31.8 (CH$_2$ in the 2'-position)-29.4 [(CH$_2$)$_5$ in the aldehyde chain]-25 (CH$_3$ in CH$_3$CO)-22.6 (CH$_2$ in the 9'-position)-20.8 (CH$_2$ in the 3'-position)-14.0 (CH$_3$ in the 10'-position)
Elementary analysis: C %=61.00 H %=8.17 N %=3.28 O %=27.55.
molecular weight Mw=15,300 with polydispersity index of 7.14.

The molecular weight Mw is determined by gel filtration using 6 columns in series: a 5 cm long precolumn (100 Å PL gel), a 50 cm column (Shodex A 801), a 30 cm column (10$^6$ Å PL gel), a 60 cm column (100 Å PL gel) and two mixed 60 cm columns (PL gel). The chromatography is carried out in dichloromethane with a flow rate of 1.5 cc/minute. The detection is carried out by refractometry. Standard solutions of polystyrene of Mw 100 to 4.10$^6$ are used.

The product is soluble in acetone (30 to 40% by weight), ethanol (15% by weight) and dichloromethane (10% by weight).

5-Use to form a film

The chitosan obtained above (40 g) is dissolved in a mixture of ethanol/1,2-dichloroethane (50/50 by weight) (100 ml). Glycerol triacetate (feedstuffs plasticizer) (5% by weight) is added to the above solution.

The solution obtained is cast on a sheet of polyethylene. The solvent is allowed to evaporate in the open air. A film is obtained having a thickness varying from 50 to 120 microns. 8 test pieces Hz are cut out. These are subjected to tractions of 1 mm/min in an INSTROM apparatus. The following characteristics are measured:
modulus of elasticity: 230+50 MPa
breaking characteristics:
breaking strength: 1.8+0.8N
breaking strain: 6.3+1.8 MPa
elongation at break: 4.7+2%

EXAMPLE 7

Hydrolyzed chitosan (1 g) is dissolved in a 10% aqueous acetic acid solution (20 cc). The pH of the mixture is adjusted to 4.5 by adding a 5N sodium hydroxide solution. Methanol (10 cc) and then a solution of 4-hydroxy-3-methoxy-benzaldehyde (18 g) in methanol (30 cc) are added. The deep green reaction mixture is stirred for 18 hours at a temperature close to 20° C. The precipitate formed is extracted with acetone in a Soxhlet apparatus for 5 hours. After drying at 35° C. under reduced pressure, the condensation product (1.65 g) of 4-hydroxy-3-methoxy-benzaldehyde with the hydrolyzed chitosan is obtained which is acetylated under the conditions described in Example 1.

After purification, the product of general formula (I) made up of a random chain of the units of formula:

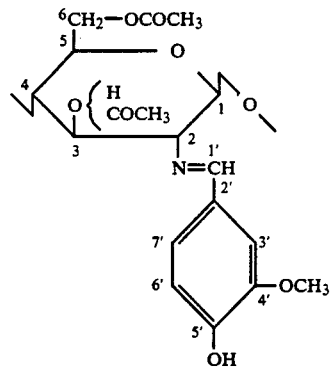

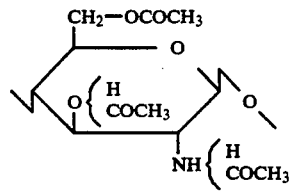

is obtained (0.990 g) which has the following characteristics:
percentage of fixation of the aldehyde: 60–65%
percentage of acetylamino: 20 to 35–40%
infrared spectrum (determination using tablets as a mixture with KBr): main characteristic absorption bands at 3400, 2945–2873, 1745–1227, 1691, 1647 and 1602–1507 cm$^{-1}$ $^{13}$C nuclear magnetic resonance spectrum (90 MHz-deuterated chloroform-shift in ppm): 170.1 (CO in the acetyl)-152 (5'-C)-151.8 (4'-C)-135.3 (2'-C)-124.6 (7'-C)-123.4 (6'-C)-111.0 (3'-C)-102.2 (1-C)-75.9 to 72.4 (2-C, 3-C, 4-C and 5-C)-62.5 (6-C)-56.1 (CH$_3$-O).

EXAMPLE 8

Previously granulated methionine (350 g) in the form of spherical particles titrating 98% and having a mean diameter of between 0.63 and 0.80 mm is coated by the fluidized bed technique ("spray coating") in a cell fitted with a WURSTER system with a solution having the following composition:

stearic acid (m.p.=68°–69° C.; acid number 194–198) 88 g
chitosan modified in accordance with Example 1:22 g
dichloromethane 500 cc
ethanol 500 cc The solution, kept at 28° C., is pulverized in the course of 60 minutes.

Granules (449 g) titrating 75% of methionine are thus obtained.

EXAMPLE 9

Previously granulated lysine hydrochloride (350 g) in the form of spherical particles having a mean diameter close to 0.8 mm is coated by the fluidized bed technique in a cell fitted with a WURSTER system with a solution having a composition identical to that described in Example 8.

The solution, kept at 29° C., is pulverized in the course of 1 hour 34 minutes.

Granules (448 g) titrating 70% of lysine hydrochloride are thus obtained.

To demonstrate the sensitivity of the coating compositions to variations in pH, tests are used which enable the release of the active substance to be measured as a function of time at different pH values and in particular at pH=6 and at pH=2.

For example, the salting out of the active substance present in the coated granules is examined by stirring, under specific conditions, a known amount of granules in the buffered medium held at constant pH at a temperature of 40° C. The release kinetics of a sample are compared at different pH values and more particularly at pH=6 and at pH=2.

The results obtained with the granules which are the subject of Examples 8 and 9 are collated in Table 3.

TABLE 3

|  |  | % of active substance released | | | | | | | |
|---|---|---|---|---|---|---|---|---|---|
|  |  | at pH = 6 after | | | at pH = 2 after | | | | |
| Examples | Titer of active substance | 1 h | 6 h | 24 h | 15 min | 1 h | 2 h | 3 h | 5 h |
| 8 | 75% (methionine) | 0 | 1.2 | 3.0 | 0.7 | 1.1 | 7.3 | 44 | 100 |
| 9 | 70% (lysine hydrochloride) | 2.7 | 10.0 | 20.0 | 1.2 | 3.4 | 37 | 100 | |

The in vivo efficacy of the coating compositions according to the invention can be demonstrated in the following test:

Samples of coated granules (approximately 0.5 g) are introduced into nylon sachets having a mesh of 300×300 microns. The sachets are placed in the rumen of fistulous ewes for 6 hours, 15 hours and 24 hours. The sachets are recovered and washed. The amount of active substance present in the sachets is determined by an appropriate method.

The results obtained are collated in Table 4.

TABLE 4

| Residence time in the rumen | % of residual methionine Product from Example 8 | % of residual lysine Product of Example 9 |
|---|---|---|
| 6 | 99 ± 1 | — |
| 15 | 98.7 ± 1 | 71 ± 7 |
| 24 | 96.8 ± 0.6 | 67.5 ± 2.5 |

We claim:

1. An organosoluble chitosan derivative which consists of a random chain of units of formulae:

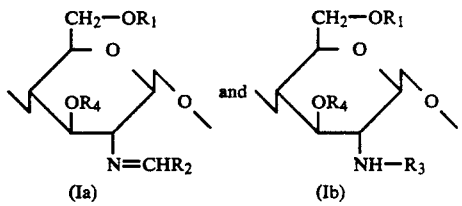

in which:
R$_1$ represents an alkylcarbonyl radical containing 2 to 4 carbon atoms,
R$_2$ represents an alkyl radical containing 2 to 21 carbon atoms or a phenyl radical which is unsubstituted or substituted by one or more identical or different radicals selected from the group consisting of hydroxyl and alkoxy,
R$_3$ represents a hydrogen atom, or an alkylcarbonyl radical containing 2 to 4 carbon atoms, and
R$_4$ represents a hydrogen atom or an alkylcarbonyl radical containing 2 to 4 carbon atoms.

2. A chitosan derivative according to claim 1, wherein the derivative has an average molecular weight of between 10,000 and 110,000.

3. A chitosan derivative according to claim 1, wherein the derivative has an average molecular weight between 10,000 and 25,000.

4. A chitosan derivative according to claim 1, wherein the derivative contains: 60 to 100% of units of the formula (Ia) and 0 to 40% of units of the formula (Ib).

5. A chitosan derivative according to claim 1, wherein R$_1$ and R$_3$ represent acetyl.

6. A chitosan derivative according to claim 1, wherein R$_2$ represents an alkyl group having 5 to 12 carbon atoms.

7. A chitosan derivative according to claim 1, wherein R$_4$ is identical to R$_1$.

8. A process for the preparation of the chitosan derivative consisting of a random chain of units of formulae:

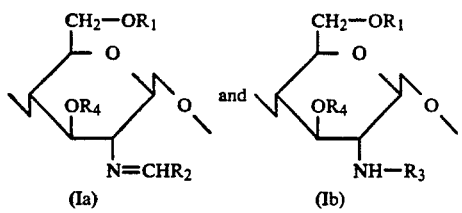

in which:

R₁ represents an alkylcarbonyl radical containing 2 to 4 carbon atoms,

R₂ represents an alkyl radical containing 2 to 21 carbon atoms or a phenyl radical which is unsubstituted or substituted by one or more identical or different radicals selected from the group consisting of hydroxyl and alkoxy, R₃ represents a hydrogen atom, or an alkylcarbonyl radical containing 2 to 4 carbon atoms, and R₄ represents a hydrogen atoms or an alkylcarbonyl radical containing 2 to 4 carbon atoms, which process comprises:

in a first step, hydrolyzing a chitosan which has been deacetylated by more than 80%;

in a second step condensing an aliphatic or aromatic aldehyde of formula R₂CHO, wherein R₂ represents the radicals as set forth above, with the chitosan obtained from the first step, and in a third step, esterifying the chitosan obtained from the second step with an acid of formula R₁—OH or derivative thereof, where R₁ represents the radicals as set forth above.

9. Process according to claim 8, wherein the hydrolysis is carried out with a strong acid selected from the group consisting hydrochloric acid, sulphuric acid, nitric acid and supported mineral acids.

10. Process according to claim 8, wherein one liter of acid having an acidity of 0.5 to 1N is used for each 25 to 50 g of chitosan to be hydrolyzed.

11. Process according to claim 8, wherein the hydrolysis is carried out at a temperature of between 80° and 120° C.

12. Process according to claim 8, wherein the aldehyde used in the second step is of the formula R₂—CHO (II) in which R₂ represents an alkyl group having 3 to 14 carbon atoms or a phenyl group substituted by a hydroxyl group or methoxy group or a hydroxyl group and a methoxy group.

13. Process according to claim 8, wherein the second step is carried out in an aqueous-alcoholic solvent.

14. Process according to claim 8, wherein the condensation reaction is carried out at a pH of between 5.5 and 6.

15. Process according to claim 8, wherein the molar ratio of the aldehyde to the average oside monomer unit of the hydrolyzed chitosan is greater than 15.

16. Process according to claim 15, wherein the molar ratio of average oside monomer unit of the hydrolized chitosan is about 20.

17. Process according to claim 8, wherein the condensation reaction is carried out at a temperature of between 10° and 50° C.

18. Process according to claim 17, wherein the condensation is carried out at 10° to 30° C.

19. Process according to claim 8, wherein the third step is carried out with an acid or an acid derivative of formula:

$$(R\ CO)_n A \qquad (III)$$

in which n is 1 or 2,

A is a hydroxyl group or a halogen when n=1,

A is oxygen when n is 2, and

R represents an alkyl group having 1 to 3 carbon atoms.

20. Process according to claim 19, wherein the acid derivative of formula (III) is acetic anhydride or acetyl chloride.

21. Process according to claim 8, wherein the condensation reaction is carried out in pyridine.

22. A method of using a chitosan according to claim 1 in cosmetology, for complexing metals, or in the preparation of film, fibres or coatings.

23. A composition for coating feedstuff additives or biologically active substances for feeding ruminants, which is stable at a pH greater than 5 and which permits the release of the additive or active substance at a pH lower than 3.5, which contains, as a substance sensitive to variations in pH, a chitosan derivative according to claim 1.

24. A composition according to claim 23, wherein the chitosan derivative in association with a hydrophobic substance has a melting point greater than 60° C.

25. Coated granules comprising a nucleus of active substance surrounded by a continuous film of a coating composition containing, as a substance sensitive to variations in pH, an organosoluble derivative of chitosan as defined in claim 1.

26. Coated granules comprising a nucleus of active substance surrounded by a continuous film of a coating composition according to claim 24.

27. Coated granules according to claim 25, wherein the active substance is a medicament, vitamin or essential amino acid.

28. Coated granules according to claim 27, wherein the active substance is methionine or lysine.

* * * * *